United States Patent [19]

Rexroth

[11] 4,427,007

[45] Jan. 24, 1984

[54] UNIVERSAL POWER COMPRESS

[76] Inventor: Thomas A. Rexroth, 522 Melville, West Burlington, Iowa 52655

[21] Appl. No.: 66,923

[22] Filed: Aug. 16, 1979

[51] Int. Cl.³ .............................................. A61B 17/12
[52] U.S. Cl. ..................................... 128/325; 128/105
[58] Field of Search ............... 128/327, 326, 325, 346, 128/133, 134, 165, 105, 99, 95; 24/248 R, 248 B, 248 E, 132 AA; 251/9, 10

[56] References Cited

U.S. PATENT DOCUMENTS

| 678,943 | 7/1901 | Davis ................................... | 128/346 |
| 2,847,014 | 8/1958 | Cohen ................................... | 128/327 |
| 3,866,611 | 2/1975 | Baumrucker ......................... | 128/346 |

FOREIGN PATENT DOCUMENTS 258945  4/1913  Fed. Rep. of Germany ...... 128/327

*Primary Examiner*—Michael H. Thaler
*Attorney, Agent, or Firm*—Wm. T. Metz

[57] ABSTRACT

A universal power compress comprised of two slightly flexible members hinged together at one end, one member having a pressure plate attached thereto and the other member having padding attached to it. A mechanism to fasten the opposite ends of the members together to hold the power compress in such a position after the members have been placed on a portion of a human body so as to apply pressure to an open wound in the human body without completely reducing the blood circulation to the surrounding areas of the human body or to the ends of a human extremity outward from the universal power compress. A bandage or gauze cover may be placed on the pressure plate to prevent contamination of the wound.

2 Claims, 8 Drawing Figures

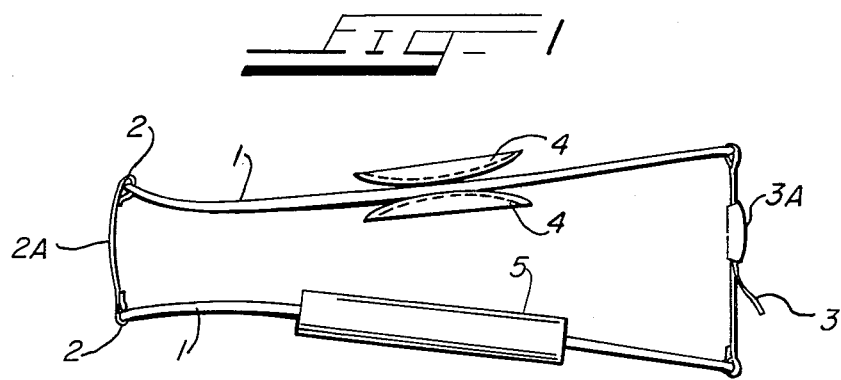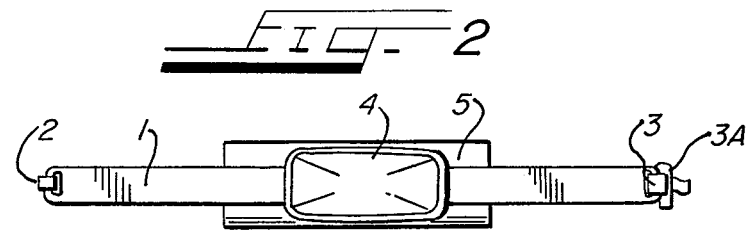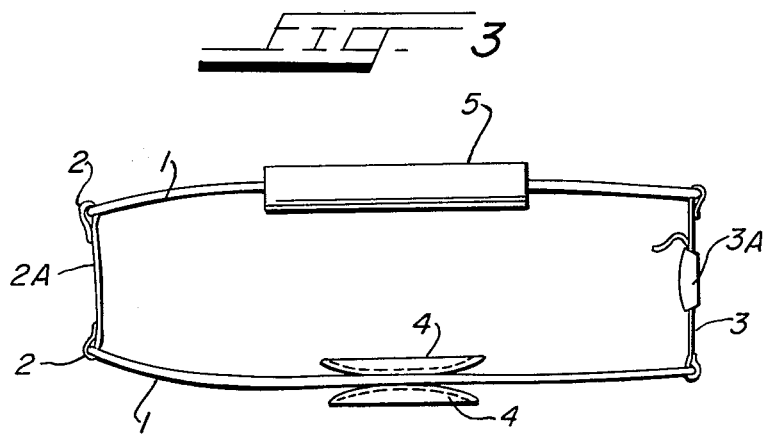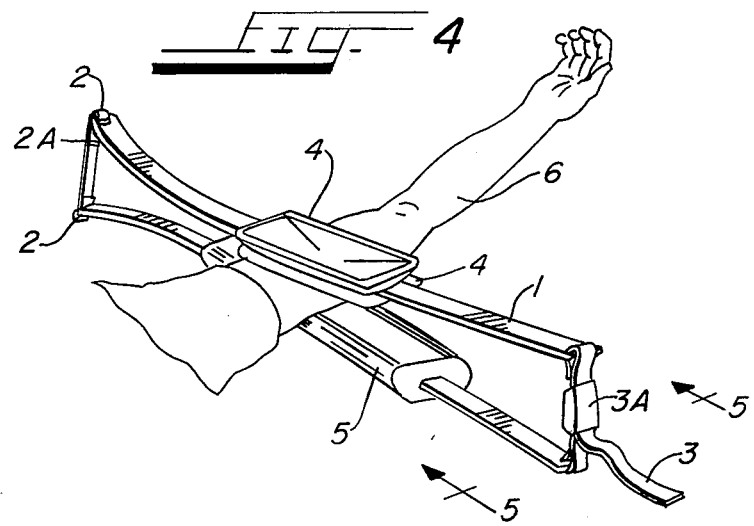

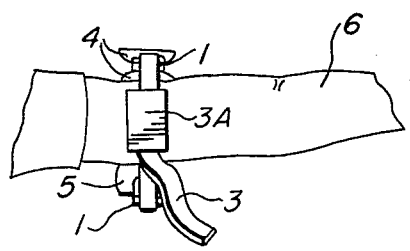
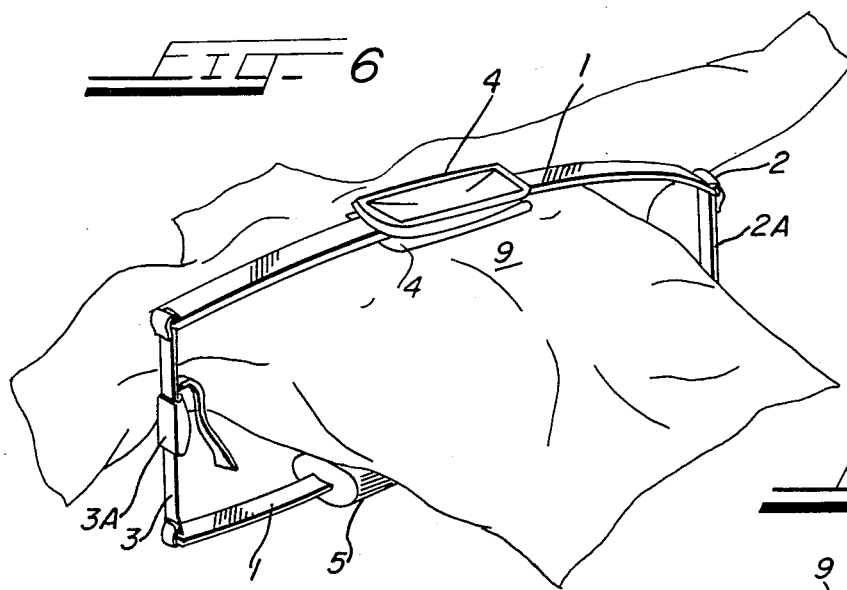
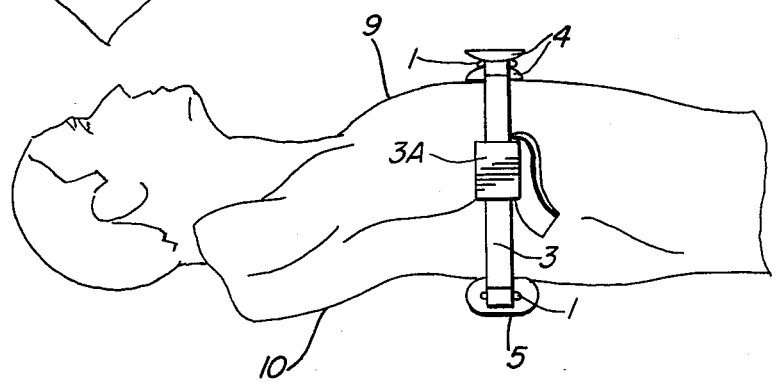
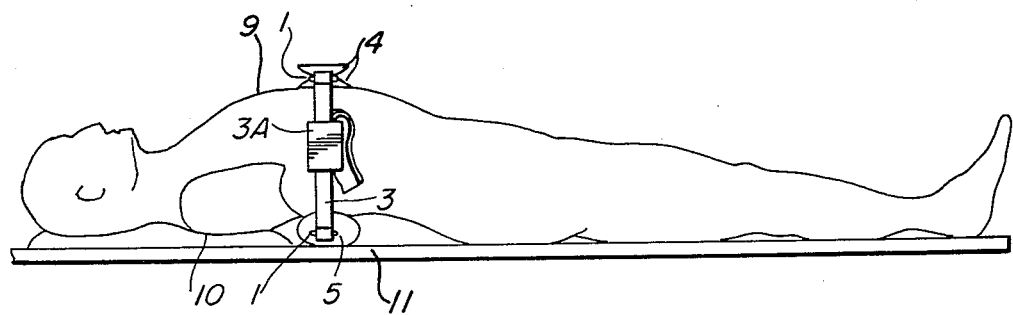

UNIVERSAL POWER COMPRESS

BACKGROUND OF THE INVENTION

1. Field of the Invention

This invention pertains to a means to stop the flow of blood from a wound by the use of pressure applied upon a bandage or compress over the wound. Means to stop the flow of blood from a wound have been known but no quick and efficient means has been devised to be used in emergency situations. Those that have been in use are cumbersome and complicated to handle and use. The universal power compress can be quickly applied to stop bleeding and easily removed to examine the wound. When applied the universal compress will stop the flow of blood from the wound without stopping the flow of blood to the surrounding areas of the human body to which it has been applied or to the ends of a human extremity outward from the universal power compress.

2. Description of the Prior Art

The following U.S. patents are in the opinion of the inventor, upon advice of counsel, the closest prior art of which the inventor is aware:

Burton—U.S. Pat. No. 575,103
Tyvand—U.S. Pat. No. 1,824,516
Pearson—U.S. Pat. No. 2,618,270
Koessler—U.S. Pat. No. 3,147,754
Bialick—U.S. Pat. No. 3,203,421

By reference to the above patents it can be seen that none anticipate or disclose the invention disclosed herein.

SUMMARY OF THE INVENTION

The universal power compress disclosed herein provides a means to stop the flow of blood from a wound and has the advantage of not cutting off circulation to the injured extremity as would a tourniquet.

It is, therefore, an object of this invention to provide a universal power compress which can be quickly and easily applied to a wound to stop bleeding and easily disengaged and removed from the wound to allow observation of the wound.

It is a further object of this invention to provide a universal power compress which will not stop the flow of blood to the injured extremity.

It is a further object of this invention to provide a universal power compress which is easily adjusted to provide only the necessary pressure to stop hemorrhaging.

It is a further object of this invention to provide a universal power compress which may be applied to the human body without having to move the body excessively.

It is a further object of this invention to provide a universal power compress which is adjustable so that it may fit either a small or large thickness of the body.

It is a further object of this invention to provide a universal power compress which is effective in first aid for a chest wound which has punctured the lung in that it will prevent sucking air into the lung and thus prevent blood from being drawn into the lung.

Further objects and advantages of this invention will become apparent from the following drawing, description and claims.

BRIEF DESCRIPTION OF THE DRAWING

FIG. 1 is a side view of the universal power compress.

FIG. 2 is a top view of the universal power compress.

FIG. 3 is a side view of the universal power compress showing it reversed for application to thicker portions of the body.

FIG. 4 is a pictorial representation of a human arm with the universal power compress attached thereto and covering a wound.

FIG. 5 is an end view of the universal power compress attached to the arm of FIG. 4 taken in the direction of the arrows 5—5.

FIG. 6 is a pictorial view of the upper portion of a human body showing the universal power compress attached over a wound in the chest.

FIG. 7 is an end view of the universal power compress attached over the wound in the chest of the human body of FIG. 6.

FIG. 8 is a side view of a human body reclining on a stretcher showing an end view of the universal power compress attached to the chest of the human body.

DESCRIPTION OF THE PREFERRED EMBODIMENT

Referring now to the drawing, the universal power compress is comprised of two slightly flexible members 1. A hinge strap 2A is connected to one end of each of the members 1 by loops 2. Flexible securing straps 3 secure the other end of the members 1 by means of a locking device 3A. Pressure plates 4 made of a hard rubber-like substance are attached to both sides of one of the members 1 and padding 5 is attached around the center of the other member 1.

The universal power compress is shown attached to a human arm 6 in FIGS. 4 and 5. Members 1 are placed with the curved portions inwardly so as to narrow the distance between the pressure plate 4 and the padding 5. The locking device 3A is then adjusted to apply pressure on a wound (not shown) in the arm 6. When the members 1 are thus fastened on either side of the human arm 6 pressure may be applied over the wound to stop bleeding. The pressure plate 4 will bend slightly to conform to the contour of the arm 6. It can be seen that the pressure from the pressure plate 4 will not cut off all of the blood circulation to the area surrounding the pressure plate 4 or to the outward portion of the arm 6.

FIGS. 6 and 7 show the universal power compress attached over a wound (not shown) in the chest 9 of a human body. The members 1 are reversed as shown in FIG. 3. The pressure plate 4 is pressed over the wound with the padding 5 against the back 10 of the human body. By adjusting the locking device 3A pressure may be applied by the pressure plate 4 over the wound. If the wound has punctured the chest cavity causing a sucking wound, the universal power compress can help seal off the wound. In this case no gauze or bandage would be used on the pressure plate 4.

Gauze and bandages (not shown) may be easily applied over the wound with the universal power compress holding them in place. The main function of this device is to stop bleeding from the human body during emergency periods while the body is being transported to places where permanent treatment may be administered to the wounded portions of the human body.

FIG. 8 shows a human body reclining on a stretcher 11. The universal power compress has been placed over a wound in the chest 9 of the human body in the manner described above.

When not in use the universal power compress may be stored in an ambulance or other place where emergency treatment is given by hanging the power compress on a hook (not shown). This may be accomplished by engaging the hinge strap 2A with the hook (not shown). The universal power compress thus hangs in a convenient fashion for ready accessability to persons administering first aid to injured persons.

I claim:

1. A universal power compress comprised of a slightly curved and slightly flexible first member, a slightly curved and slightly flexible second member, a flexible hinge strap pivotably connecting one end of the first member to one end of the second member, a pressure plate attached to one side of the first member, a second pressure plate attached to the opposite side of the first member, padding surrounding a portion of the second member, a flexible locking strap pivotably attached to the first member, a second flexible locking strap pivotably attached to the second member and an adjustable locking device connecting the flexible locking straps.

2. The universal power compress of claim 1, the pressure plates being a hard slightly bendable rubber-like substance.

* * * * *